US007772556B2

(12) United States Patent
Reddy et al.

(10) Patent No.: US 7,772,556 B2
(45) Date of Patent: Aug. 10, 2010

(54) DETECTION SYSTEM FOR DETECTING AN ANALYTE IN A FLUID MEDIUM

(75) Inventors: C. V. Gopal Reddy, Glen Allen, VA (US); Carl P. Tripp, Orono, ME (US)

(73) Assignee: University Of Maine System Board Of Trustees, Bangor, ME (US)

( * ) Notice: Subject to any disclaimer, the term of this patent is extended or adjusted under 35 U.S.C. 154(b) by 0 days.

(21) Appl. No.: 11/985,107

(22) Filed: Nov. 14, 2007

(65) Prior Publication Data
US 2009/0122312 A1 May 14, 2009

(51) Int. Cl.
G01J 5/02 (2006.01)
G01N 21/62 (2006.01)

(52) U.S. Cl. .................. 250/339.07; 436/171
(58) Field of Classification Search ............ 250/339.07, 250/338.14, 339.11, 336.1; 356/451; 436/171
See application file for complete search history.

(56) References Cited

U.S. PATENT DOCUMENTS

| | | | |
|---|---|---|---|
| 2,194,438 | A | 3/1940 | Wernlund et al. |
| 3,650,949 | A | 3/1972 | Hager et al. |
| 4,091,822 | A | 5/1978 | Ihrig et al. |
| 4,756,804 | A | 7/1988 | Driscoll et al. |
| 4,763,674 | A | 8/1988 | Lelah |
| 5,112,494 | A | 5/1992 | Yan |
| 6,001,240 | A | 12/1999 | Dorisio Deininger et al. |
| 6,074,539 | A | 6/2000 | Dorisio Deininger et al. |
| 7,186,379 | B2 | 3/2007 | Rosentreter et al. |
| 2003/0089855 | A1* | 5/2003 | Strauss et al. ........... 250/339.07 |
| 2004/0046121 | A1* | 3/2004 | Golden et al. .......... 250/339.07 |
| 2004/0094705 | A1* | 5/2004 | Wood et al. .................. 250/288 |
| 2005/0037514 | A1 | 2/2005 | Carron et al. |
| 2005/0040328 | A1* | 2/2005 | Donegan et al. ............. 250/288 |
| 2005/0266583 | A1* | 12/2005 | Farquharson et al. ....... 436/171 |
| 2007/0084996 | A1* | 4/2007 | Li et al. ...................... 250/282 |
| 2008/0073505 | A1* | 3/2008 | Niu et al. .................... 250/288 |

OTHER PUBLICATIONS

G. Muller et al., Real-Time ATR-IR Spectroscopy of Samples on Exchangeable Composite Reflection Elements, Applied Spectroscopy, vol. 53, No. 12, 1999, pp. 1551-1555.
M. Allmendinger et al., Online ATR-IR Investigations and Mechanistic Understanding of the Carbonylation of Epoxides—The Selective Synthesis of Lactones or Polyesters From Epoxides and CO, Journal of Organometallic Chemistry, vol. 689, Issue 5, Mar. 1, 2004, pp. 971-979.
G.W. Somsen et al., Liquid Chromatography-Fourier-Transform Infrared Spectrometry, Journal of Chromatography A, vol. 856, Issues 1-2, Sep. 24, 1999, pp. 213-242.
Rafael Lucena et al., ATR-FTIR Membrane-Based Sensor for the Simultaneous Determination of Surfactant and Oil Total Indices in Industrial Degreasing Baths, Department of Analytical Chemistry, 2006, vol. 131, No. 3, pp. 415-421.
International Search Report and Written Opinion, PCT/US2008/083473, Mar. 31, 2009.

* cited by examiner

*Primary Examiner*—David P Porta
*Assistant Examiner*—Faye Boosalis
(74) *Attorney, Agent, or Firm*—MacMillan, Sobanski & Todd, LLC

(57) ABSTRACT

This invention relates to a detection system for detecting an analyte in a fluid medium. The detection system comprises a substrate that provides mechanical stability and is sized and shaped to intercept an infrared beam. A reactive material is coated on the substrate. When contacted with the analyte in the fluid medium, the reactive material reacts with the analyte and is altered. The detection system also comprises an infrared spectrometer producing the infrared beam that passes through the reactive material to a detector of the spectrometer. The alteration of the reactive material allows the spectrometer to identify and quantify the analyte. In one embodiment, the reactive material irreversibly reacts with the analyte. In another embodiment, the spectrometer is a non-ATR infrared spectrometer. In a further embodiment, the substrate is a disposable substrate.

21 Claims, 4 Drawing Sheets

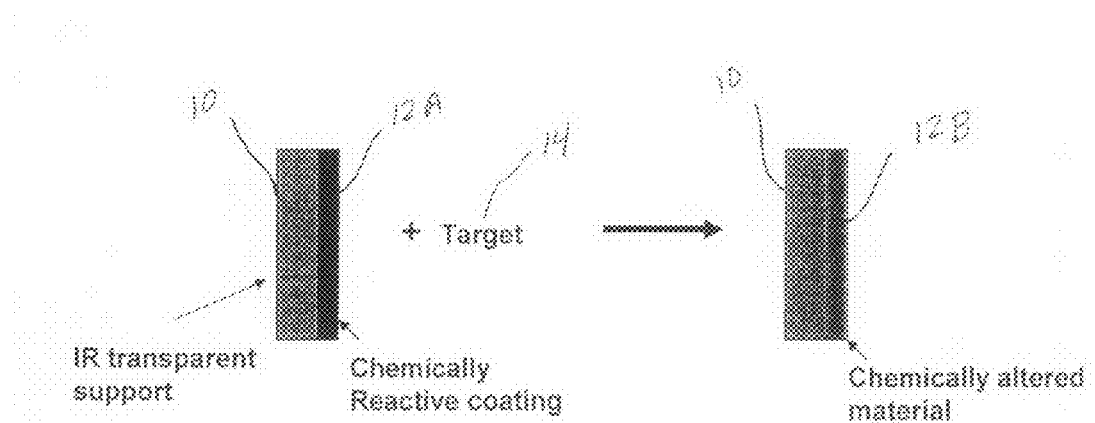
Figure 1: Chemically Reactive Supports Used with Transmission IR Spectroscopy
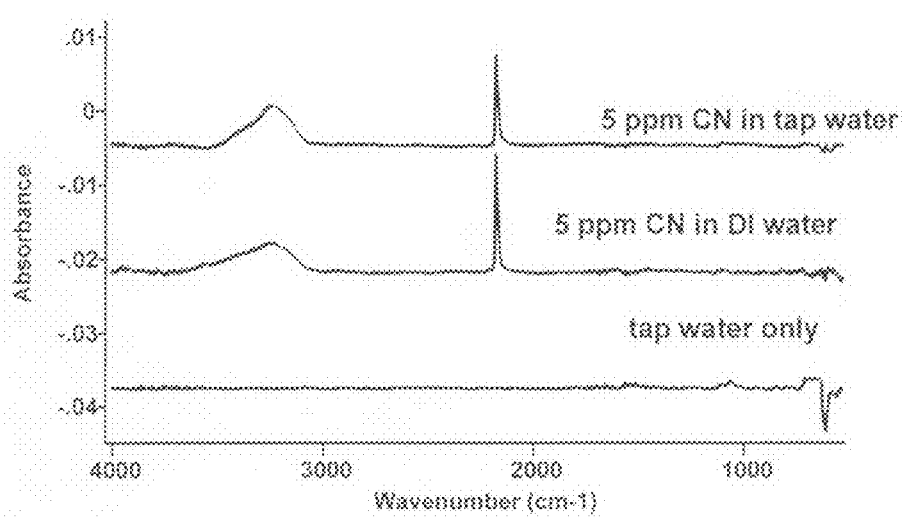
Figure 2: IR Spectra of CuI Films Exposed to Tap Water Only and Exposed to 5 ppm NaCN Solutions in Deionized and Tap Water

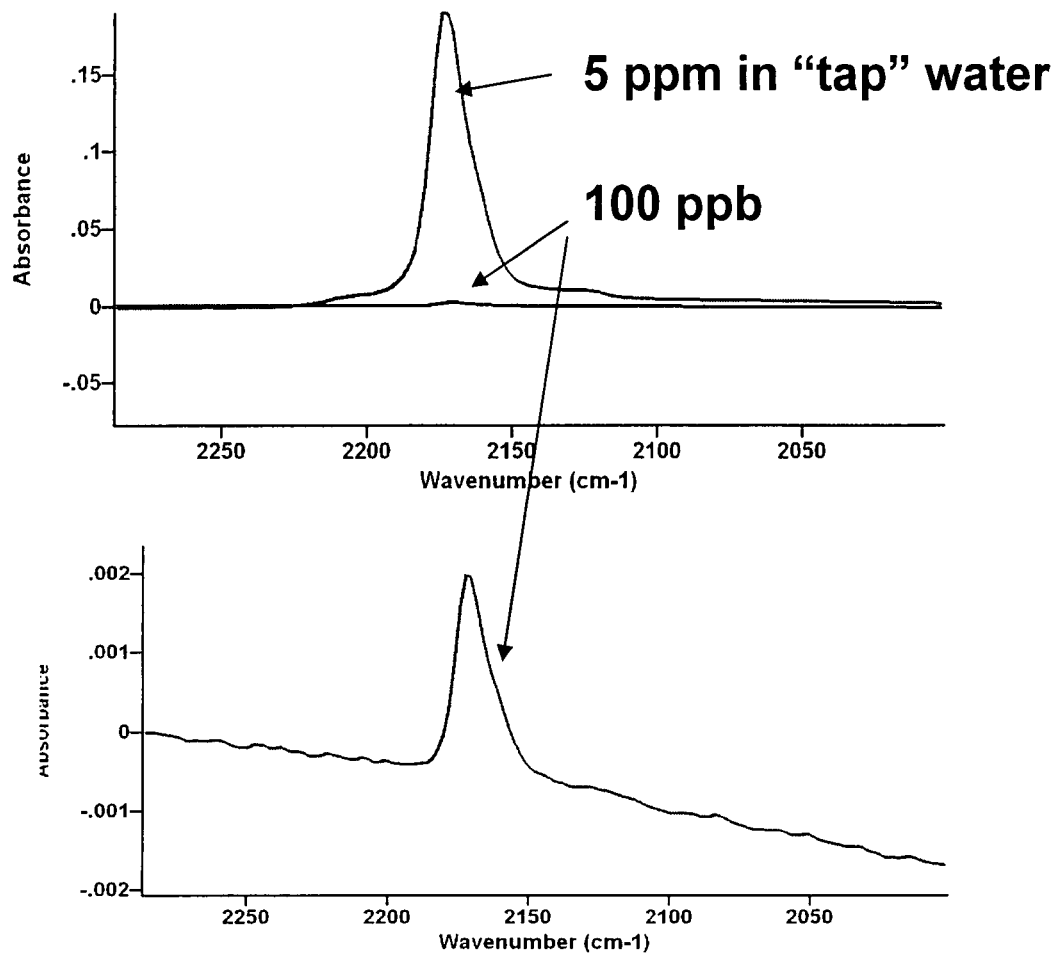
Figure 3: IR Spectra of CuI/Si Films Exposed to 5 ppm and 100 ppb NaCN in Tap Water

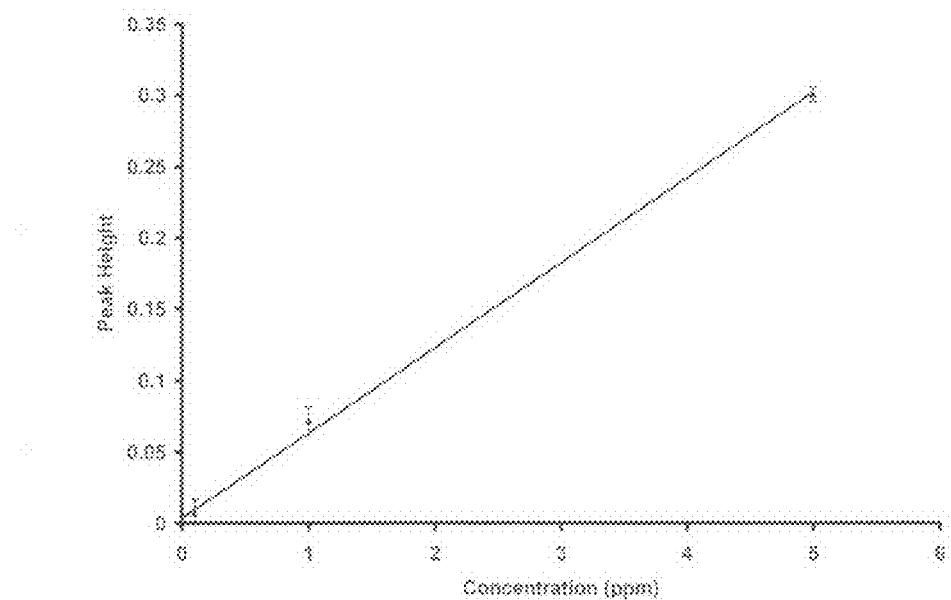
Figure 4: Peak Height of the 2273 cm$^{-1}$ Band vs Cyanide Concentration in Tap Water
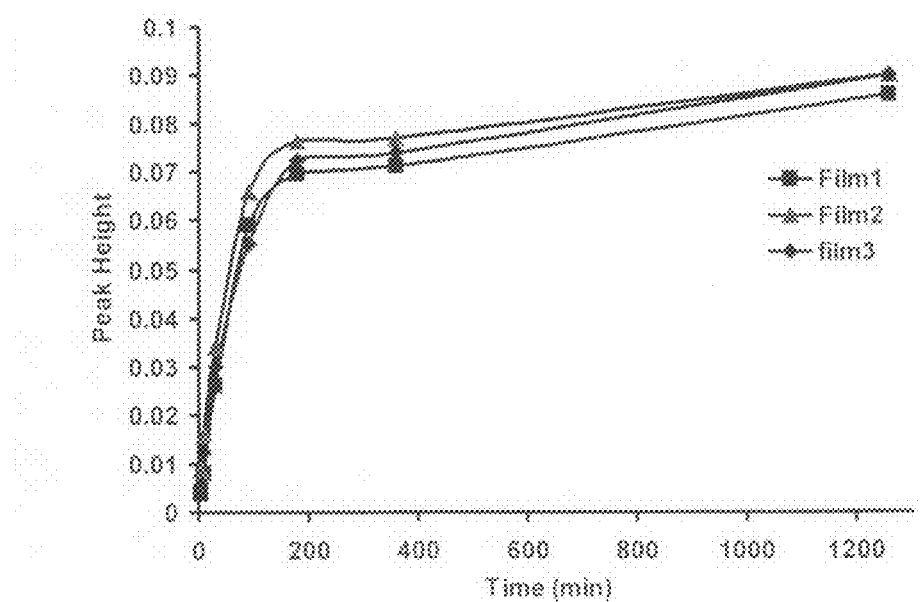
Figure 5: Peak Height vs Incubation Time to a 1 ppm Cyanide Solution for CuI Films of Different Thicknesses

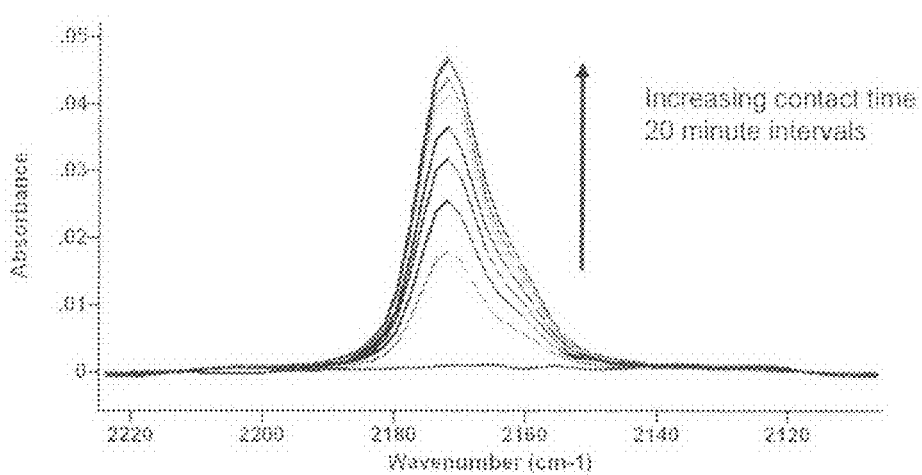
Figure 6: IR Spectrum of CuI Coated ATR Exposed to a Flowing Solution of a 50 ppm NaCN Solution in DI Water
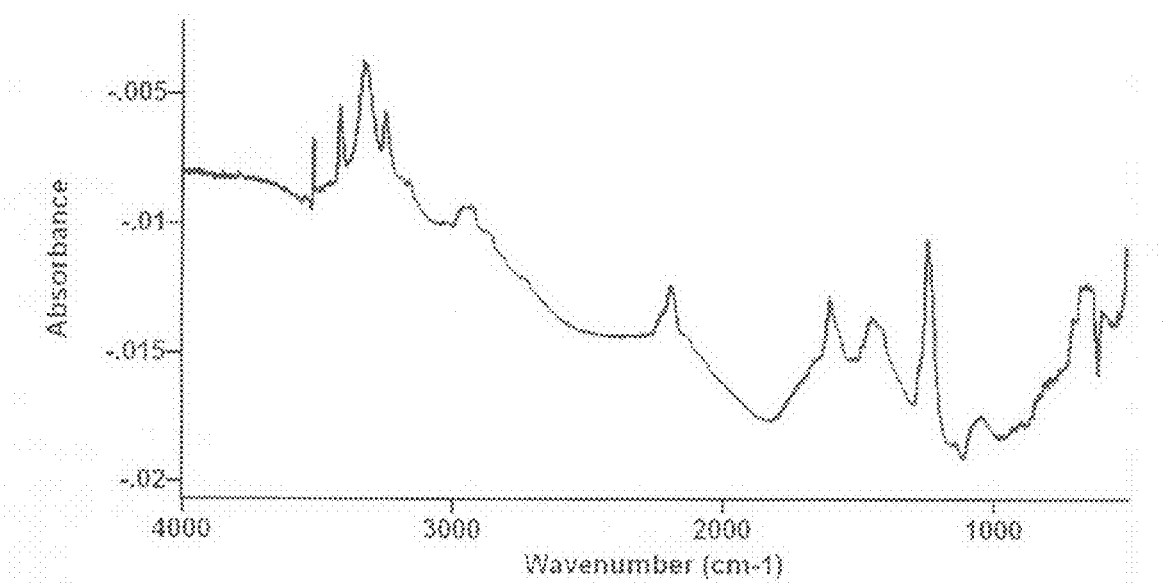
Figure 7: IR Spectrum of a CuBr Film Exposed to 5 Second Pulse of Cigarette Smoke

US 7,772,556 B2

DETECTION SYSTEM FOR DETECTING AN ANALYTE IN A FLUID MEDIUM

BACKGROUND OF THE INVENTION

This invention relates in general to systems and methods for detecting analytes in fluid mediums, and in particular to a system that may be used to detect analytes such as chemical compounds and microorganisms in air and in water.

Hydrogen cyanide is a highly toxic compound produced in large quantities by industrial processes, automobile exhaust and cigarette smoke. In the year 2000, 1615 million pounds were produced in the US. The toxicity is caused by the cyanide ion, which prevents cellular respiration. An HCN concentration of 300 parts per million in air is lethal to humans within a few minutes.

Currently there exists a critical need within the military and homeland defense for sensors and detection systems that are capable of identifying and quantifying agents such as HCN. In addition, monitoring of HCN generated from industrial activities is a persistent concern within private and public settings.

Drinking water can be analyzed for cyanide using volumetric titration or colorimetry. Other methods include absorption spectrophotometry, ion-selective electrodes, indirect atomic absorption spectrophotometry, fluorometry and gas chromatography. There is still a need for an improved system for detecting cyanide and other analytes in fluid mediums.

SUMMARY OF THE INVENTION

This invention relates to a detection system for detecting an analyte in a fluid medium. The detection system comprises a substrate that provides mechanical stability and is sized and shaped to intercept an infrared beam. A reactive material is coated on the substrate. When contacted with the analyte in the fluid medium, the reactive material irreversibly reacts with the analyte and is altered. The detection system also comprises an infrared spectrometer producing the infrared beam that passes through the reactive material to a detector of the spectrometer. The alteration of the reactive material allows the spectrometer to identify and quantify the analyte.

In another embodiment, the invention relates to a detection system for detecting an analyte in a fluid medium. The detection system comprises a substrate that provides mechanical stability and is sized and shaped to intercept an infrared beam. A reactive material is coated on the substrate. When contacted with the analyte in the fluid medium, the reactive material reacts with the analyte and is altered. The detection system also comprises a non-ATR infrared spectrometer producing the infrared beam that passes through the reactive material to a detector of the spectrometer. The alteration of the reactive material allows the spectrometer to identify and quantify the analyte.

In a further embodiment, the invention relates to a detection system for detecting an analyte in a fluid medium. The detection system comprises a disposable substrate that provides mechanical stability and is sized and shaped to intercept an infrared beam. A reactive material is coated on the substrate. When contacted with the analyte in the fluid medium, the reactive material reacts with the analyte and is altered. The detection system also comprises an infrared spectrometer producing the infrared beam that passes through the reactive material to a detector of the spectrometer. The alteration of the reactive material allows the spectrometer to identify and quantify the analyte.

Various aspects of this invention will become apparent to those skilled in the art from the following detailed description of the preferred embodiments, when read in light of the accompanying drawings.

BRIEF DESCRIPTION OF THE DRAWINGS

FIG. 1 is a schematic view of part of a system for detecting an analyte in a fluid medium according to the invention, showing a substrate coated with a reactive material before and after the reactive material is contacted with a target analyte.

FIG. 2 shows the infrared spectra of copper iodide films coated on silicon chips and exposed to tap water (control), and 5 ppm sodium cyanide in tap water and in distilled water.

FIG. 3 shows the infrared spectra of copper iodide films coated on silicon chips and exposed to 5 ppm and 100 ppb sodium cyanide in tap water.

FIG. 4 is a plot of the peak height of an infrared spectroscopy band for cyanide versus the concentration of the cyanide in tap water, demonstrating that the detection system can be used to quantitatively determine the concentration of cyanide in solution.

FIG. 5 is a plot of the peak height of an infrared spectroscopy band for cyanide versus incubation time to a 1 ppm cyanide solution for copper iodide films of different thicknesses, demonstrating that the difference in film thickness did not significantly affect the peak height.

FIG. 6 shows the infrared spectra of a cupper iodide film coated on an ATR crystal and exposed to a flowing solution of a 50 ppm sodium cyanide solution in distilled water with increasing contact time at 20 minute intervals.

FIG. 7 shows the infrared spectrum of a copper bromide film coated on a silicon chip and exposed to a 5 second pulse of cigarette smoke that contains cyanide.

DETAILED DESCRIPTION OF THE PREFERRED EMBODIMENTS

The detection system of the invention uses a reactive material coated on a substrate, in combination with infrared spectroscopic analysis, to detect an analyte in a fluid medium. The substrate provides mechanical stability to the combination of the substrate and the reactive material. The substrate may also provide ease of handling of the combination. FIG. 1 shows an example of a substrate 10 coated with a reactive material 12A.

Any suitable material(s) can be used to make the substrate. The material used may depend on which of the different infrared spectroscopy modes is used in the detection system, such as transmission, specular reflection, diffuse reflectance (DRIFT), Attenuated Total Reflection (ATR), photoacoustic or emission. For infrared spectroscopy in transmission mode, the material used to make the substrate is at least partially transparent in the spectral region of interest. For example, materials such as polymers, metal oxides and metal salts, as well as common infrared window materials such as silicon can be used. Infrared spectroscopy in photoacoustic and reflection modes can use the above-mentioned materials and can also use opaque and/or reflective materials such as metals for the substrate. ATR infrared spectroscopy uses an internal reflection element called a crystal as the substrate, which can be made from any suitable material such as Si, Ge, ZnSe, ZnS, diamond, sapphire, $CaF_2$ or $BaF_2$.

The substrate is sized and shaped to intercept an infrared beam from the spectrometer. The size and shape of the substrate may vary considerably depending on the infrared spectroscopy mode used in the detection system. In one embodiment the substrate is disposable and not reused as part of the spectroscopy method. For example, a disposable substrate for use in an infrared transmission mode may be a square or rectangular shaped chip or wafer having an area within a range of from about 0.1 mm$^2$ to about 10 cm$^2$ and a thickness within a range of from about 25 um to about 5 cm. The substrate may be sized and shaped for mounting in a standard transmission holder of an infrared spectrometer. The substrate 10 shown in FIG. 1 is a square shaped disposable chip.

Alternatively, a crystal used as the substrate for ATR infrared spectroscopy may have an elongated rectangular shape with beveled ends. The crystal can have any suitable size, for example, a length within a range of from about 0.5 cm to about 10 cm, a width within a range of from about 0.1 cm to about 3 cm, and a thickness within a range of from about 0.1 cm to about 1 cm.

The surface of the substrate may be coated with an adhesive layer (not shown) to increase the robustness of the coating of reactive material to flowing water solutions, or the substrate may be roughened to increase adhesion as well as increase the surface area of the coating. In one embodiment, a high surface area material coating such as a mesoporous silica film or porous polymer layer is applied to the substrate to increase the surface area of the reactive coating exposed to the analyte. In another embodiment, the substrate is porous to allow a gaseous stream or water based solutions to pass through the substrate.

The reactive material coated on the substrate, when contacted with the analyte in the fluid medium, reacts with the analyte and is altered. As shown in FIG. 1, a target analyte 14 comes into contact with the reactive material 12A on the substrate 10. As indicated to the right of the arrow in the figure, the reactive material 12B has been altered by reaction with the analyte. This can be any type of reaction that results in alteration of the reactive material, such as a chemical, biochemical or electrochemical reaction depending on the nature of the analyte and the reactive material. The reaction can be irreversible or reversible. In one embodiment, the reactive material irreversibly reacts with the analyte; this excludes reactive materials that can be activated and deactivated a number of times for reuse. In one embodiment, the reactive material forms a covalent bond between the reactive material and the analyte. A reactive material is chosen for use that reacts with the analyte or class of analytes of interest. Detection and identification of the specific analyte(s) is then provided by infrared spectroscopy.

Any suitable reactive material or combinations of different reactive materials can be coated on the substrate. The reactive material is infrared amenable. In one embodiment, for water based detection, the reactive material is insoluble in water before and after reacting with the analyte. In some embodiments the reactive material is a metal salt. In the case of HCN or CN$^-$ detection in water, various metal salts including metal halides, nitrates, acetates, carbonyls, sulfides, or oxides could be used. In a particular embodiment, the reactive material is a metal halide, and more particularly a copper halide such as CuI or CuBr. Both salts have no IR bands in the mid-IR region and have $K_{sp}$ of $1.27 \times 10^{-12}$ and $6.27 \times 10^{-9}$, respectively. Furthermore, CN$^-$ is highly reactive with CuI forming CuCN with a $K_{sp} = 3.47 \times 10^{20}$.

The reactive material is coated on the substrate by any suitable means. "Coated" refers to attachment by any physical or chemical means. For example, deposition of the reactive material on the substrate can be accomplished using standard methods such as pressing the dry material or dry material with a suitable binder on the substrate or wet methods such as casting, spraying or spin coating. The reactive material may also be deposited on the substrate using chemical/physical deposition or vacuum sublimation techniques.

The coating of reactive material can have any suitable thickness, which can vary widely depending on a particular application. In one embodiment, the reactive material forms a relatively thin coating or film on the substrate. For example, the reactive material may form a coating on the substrate having a thickness within a range of from about 1 nanometer to about 20 microns, and more particularly from about 0.2 micron to about 10 microns.

Any suitable infrared spectroscopy technique can be used as part of the detection system, such as any of those well known in the art. In brief, infrared spectroscopy is the absorption measurement of different IR frequencies by a sample positioned in the path of an IR beam. The main goal of IR spectroscopic analysis is to determine the chemical functional groups in the sample. Different functional groups absorb characteristic frequencies of IR radiation. IR spectra are obtained by detecting changes in transmittance (or absorption) intensity as a function of frequency.

Most commercial instruments separate and measure IR radiation using dispersive spectrometers or Fourier transform spectrometers. In a typical dispersive IR spectrometer, radiation from a broad-band source passes through the sample and is dispersed by a monochromator into component frequencies. Then the beams fall on the detector, which generates an electrical signal and results in a recorder response. Fourier transform spectrometers have recently replaced dispersive instruments for most applications due to their superior speed and sensitivity. Instead of viewing each component frequency sequentially, as in a dispersive IR spectrometer, all frequencies are examined simultaneously in Fourier transform infrared (FTIR) spectroscopy. The three basic spectrometer components in an FT system are a radiation source, an interferometer and a detector.

Specular reflectance is a mode of IR spectroscopy that involves a mirrorlike reflection and produces a reflection-absorption spectrum for a surface film of the sample on a reflective surface. Diffuse reflectance is another mode of IR spectroscopy in which IR radiation is focused onto the surface of a sample and results in two types of reflections: specular reflectance, which directly reflects off the surface and has equal angles of incidence and reflectance, and diffuse reflectance, which penetrates into the sample, then scatters in all directions. Reflection accessories are designed to collect and refocus the resulting diffusely scattered light while minimizing the specular reflectance which distorts the IR spectra. This technique is often called diffuse reflectance infrared Fourier transform spectroscopy (DRIFT).

In photoacoustic spectroscopy (PAS) the modulated IR radiation from an FTIR interferometer is focused on a sample placed inside a chamber containing an IR-transparent gas. IR radiation absorbed by the sample converts into heat inside the sample. The heat diffuses to the sample surface, then into the surrounding gas atmosphere, and causes expansion of a boundary layer of gas next to the sample surface. Thus, the modulated IR radiation produces intermittent thermal expansion of the boundary layer and generates pressure waves which are detected by a microphone.

Emission spectroscopy is another technique in which the sample is heated to an elevated temperature, emitting enough energy in the infrared region to be detected by an FTIR detector. Emission spectral bands occur at the same frequencies as absorption bands.

Attenuated total reflectance (ATR) is another mode of IR spectroscopy in which the sample is placed on the surface of a dense, high refractive index crystal. The IR beam is directed onto the beveled edge of the ATR crystal and internally reflected through the crystal with a single or multiple reflections. The beam penetrates a very short distance into the sample on the surface before the complete reflection occurs. This penetration is called the evanescent wave and typically is at a depth of a few micrometers. Its intensity is reduced (attenuated) by the sample in regions of the IR spectrum where the sample absorbs. Although ATR infrared spectroscopy can be used in the detection system of the invention, one embodiment excludes the use of ATR.

The detection system can be used for detecting analytes in any type of fluid medium, which includes both gases and liquids. In some embodiments the fluid medium is aqueous.

Also, the detection system can be used for detecting many different types of analytes. The analytes could include both chemical materials and biological materials. For example, the detection system could be used as a common platform for both chemical and biowarfare agents in air and in water. In some embodiments the analyte is a chemical compound; this can be any type of chemical compound, for example cyanide as discussed above.

By combining a reactive material with the high molecular information content afforded by IR spectroscopy a high level of detection selectivity can be achieved. This is demonstrated in the following examples with the detection of HCN in cigarette smoke and in tap water. In essence, reaction of the reactive material with HCN produces a unique and intense IR band that provides high selectivity and sensitivity of detection in the presence of interferents in both aqueous and gas streams. The enhanced sensitivity arises from a process that does not rely on a surface reaction or surface adsorption process where the sensitivity depends on the surface area of the material and the density of reactive sites.

The detection method in analytical processes in general involves an initial step of concentration of the analyte using solid phase extraction. In a conventional detection system, the analyte is not bonded strongly to the support because it is eluted and presented to the instrument used for detection. In contrast, in the present detection system the infrared spectrum may be recorded directly on the material used to extract the analyte. No elution is required and this also means that the analyte can be bonded strongly with the material. Consequently, the system does not require a high surface area absorbent since bulk chemistry can be accomplished with a thin reactive film.

EXAMPLES

Example 1

Cyanide Detection in Water Using FTIR

The first example is provided to demonstrate detection of HCN or $CN^-$ in water. In this particular example, CuI was deposited as films on a Si window. A 4 in dia. Si wafer (4 mm thick, double polished) was diced into 1×1 cm squares and cleaned using UV/ozone treatment prior to use. A 4 mm thickness was chosen to avoid the appearance of interference fringes in the spectrum. A first approach to depositing a film was to cast a suspension of the copper halide on the Si wafer from acetonitrile. Films produced in this manner exhibited poor transmission due to scattering by the large particulates.

In a second approach, uniform films were deposited by thermal evaporation in an evaporation chamber using approximately 50 mg of pure CuI (99.98% from Aldrich-Sigma) in a quartz crucible under $10^{-5}$ torr pressure. The film deposition rate was about 1 nm/s and deposited films were approximately 1 μm. Films produced in this manner showed no bands across the entire IR region (4000–400 $cm^{-1}$) and no reduction in transmission compared to a bare Si chip.

The coated Si chips were immersed in 200 ml of freshly prepared solutions of NaCN in distilled water and tap water. The "tap water" was a prepared solution according to DOD standards containing the following compounds in distilled water: 100 mg/L $NaHCO_3$, 13.4 mg/L $MgSO_4.7H_2$), 27.0 mg/L $CaSO_4$, 0.7 mg/L $K_2HPO_4$, 0.3 mg/L $KH_2PO_4$, 0.01 mg/L $(NH_4)_2SO_4$, 0.01 mg/L NaCl, 0.001 mg/L $FeSO_4$, 1.0 mg/L humic acid, 1.0 mg/L fulvic acid, and 1.0 mg/L $NaNO_3$. The solution was adjusted to pH 5-6 using a dilute solution of HCl. The chip was incubated for a period of time in the stirred solution, removed and dried by gently blowing $N_2$ gas for 5 to 10 minutes. The chip changed color from a dull gray to a light green indicative of formation of CuCN. The chip was then mounted in a standard transmission holder and an IR spectrum recorded. A reference spectrum was recorded through the coated chip prior to immersion into the solution. FTIR spectra were recorded using an ABB-BOMEM FTLA 2000 spectrometer equipped with an MCT detector. The spectra were recorded at room temperature at a resolution of 4 $cm^{-1}$ with a typical collection time of 1 minute.

CuI films were robust showing no loss from the Si with stirring in aqueous solutions over a 2 day period. Films of CuBr were less robust owing to the lower $K_{sp}$ and showed some loss (5%) of material in stirred water solutions over the same 2 day period. However, the robustness of the films degraded in basic solutions. Films of CuBr were completely removed by immersion in water in 2 hrs at pH 8. This was circumvented by adjusting the pH to between 5-6.

FIG. 2 shows the spectra of the CuI thin films on Si chips exposed to a stirred beaker containing 200 ml of tap water, 5 ppm solutions of NaCN in deionized and tap water, respectively. The chips were immersed for a fixed time in the stirred beaker, removed and dried at room temperature for 5-10 minutes and then mounted in the IR transmission cell. After recording the spectrum, the chips were immersed again in the beaker for an additional time and removed again for recording the spectrum. This procedure was continued until a maximum intensity in the band due to CuCN was obtained. The spectra shown in FIG. 2 represent typical spectra obtained for the maximum band intensity when a CuI film was exposed to a 5 ppm NaCN solution.

The immersion of the chip into a solution containing tap water only is provided as a control. No bands appear when the film is exposed to only tap water showing that the interferents found in tap water do not react or adsorb to any appreciable level with the coating. This contrasts to the spectra obtained for immersion of the chips in the 5 ppm NaCN in DI water or tap water. A broad band near 3400 $cm^{-1}$ is due to water. More important, a single sharp band at 2173 $cm^{-1}$ appears in the spectrum which is stretching vibration υ(CN) of CuCN. The intensity of this band is about 0.015 absorbance in both spectra showing that the interferents present in tap water do not hinder the reaction of cyanide with the film. In addition, the peak-to-peak noise of the FTIR spectrometer in the 2000 $cm^{-1}$ region is $4\times10^{-4}$ for a 1 second scan which gives a signal-to-noise ratio of about 40:1 for detection of 5 ppm cyanide in a 1 second scan. For a 2 minute scan the signal-to-noise is approximately 10 times greater. This shows that this approach has the sensitivity for low ppb detection levels.

The Tri-Service Water Quality Standard detection limit for cyanide is 2 ppm. To demonstrate that this detection level can be achieved, the CuI coated chips were immersed in stirred beakers containing 200 ml of 100 ppb and 5 ppm NaCN solutions until a maximum in peak intensity of the CN band at 2173 cm$^{-1}$ was obtained. The spectra in FIG. 3 clearly demonstrate that detection at low ppm is achieved and that low ppb is possible. In addition, it is noted that the peak height or peak area is proportional to the concentration of cyanide in solution. FIG. 4 is a plot of the peak height vs cyanide solution concentration and shows a linear dependence with concentration. This demonstrates that this approach can be used to quantitatively determine the concentration of cyanide in solution. From the peak area, the mass of CuCN produced can be determined. For the three concentrations (100 ppb, 1 ppm and 5 ppm) used in establishing the calibration curve shown in FIG. 4, we estimate that about 20% of the cyanide in the 200 ml solution was extracted at all three concentrations.

The calibration curve in FIG. 4 was established for the maximum amount of cyanide reacting with the chip. The time required to achieve a maximum in the amount adsorbed could be due to mass transport to the chip and mass transport into the film itself. However, the curves in FIG. 5 show that mass transport into the films is not a factor. The three films analyzed are of different thicknesses. Film 2 and Film 3 are 2 and 3 times the thickness of Film 1, respectively. The three different thicknesses of the CuI film were prepared by varying the deposition time on Si substrate and are estimated to vary from 0.4 microns to 2.6 microns in thickness as determined by step profilometry. The curves in FIG. 5 show the same time dependence and the same maximum amount of CuCN formed for all three samples when immersed into 200 ml of a 1 ppm cyanide solution. For all three curves, the peak height increases with time of exposing to cyanide solution up to 300 minutes. After 300 minutes, there was no significant change in peak height. This shows that the reaction time is dictated by mass transport to chip and not to mass transport into the film. Reaction occurs with an outer film layer and once this has been achieved the CuCN acts as a protective barrier and impedes CN from penetrating into the interior of the film.

Example 2

Cyanide Detection In Water Using ATR-FTIR

The second example demonstrates the use of a reactive film deposited on an ATR crystal. The coupling of the reactive coating with ATR provides an avenue for continuous monitoring of an aqueous solution. A CuI film was vacuum deposited on a 5×1×0.2 cm silicon ATR crystal beveled at 45 degrees using the same procedure outlined in the preparation of a film on a Si chip. The film thickness can be 10 nanometers to 5 microns. The crystal was mounted in a standard flow-through cell obtained from Harrick Corp. and a reference recorded with distilled water flowing at a rate of 2 ml/min through the cell. FIG. 6 shows the spectra recorded in situ to exposure to a flowing solution of 50 ppm cyanide. A band at 2273 cm$^{-1}$ due to CuCN appears and the time dependence in the growth of this band is due to mass transport to the surface of the coating.

Example 3

Cyanide Detection In Gas Phase Using FTIR

Examples 1 and 2 demonstrate sampling arrangements for use of the reactive coatings for detecting cyanide in water. A third example shows the use of these films for detecting gaseous HCN. In this case, a film of CuBr coated on a Si chip was held above a lit cigarette for 5 seconds and the spectrum obtained after exposure is shown in FIG. 7. This figure contains a band at 2273 cm$^{-1}$ due to the formation of CuCN along with several other bands in other regions of the spectrum. Recall that the exposure of cyanide solutions in tap water did not result in additional bands arising from interferents reacting with the coated Si chip. However, cigarette smoke is known to contain over 4000 chemical compounds of which 43 are known carcinogens. HCN is one of these compounds and the amount produced per cigarette is 70-240 ug. It is not surprising that some of the other 4000 interferent compounds that are present in cigarette smoke adsorb or react with the CuBr film. Nevertheless the appearance of the band at 2273 cm$^{-1}$ is clear evidence of the reaction of HCN with the film. Furthermore, from the intensity of the band at 2273 cm$^{-1}$, it is found that approximately 2 ug of HCN has reacted with the film. This value is in the expected range of 1-4 ug HCN produced in a 5 second exposure to cigarette spoke. Thus the adsorption or reaction of interferent molecules did not interfere with quantification of the cyanide in the cigarette smoke. The spectrum in FIG. 7 clearly demonstrates the value of combining a reactive film approach with the molecular discrimination afforded by IR spectroscopy.

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. A detection system for detecting an analyte in a fluid medium comprising:
    a substrate providing mechanical stability and sized and shaped to intercept an infrared beam;
    a reactive material, coated on the substrate, that when contacted with the analyte in the fluid medium irreversibly reacts with the analyte and is altered, the reaction being a chemical, biochemical or electrochemical reaction; and
    an infrared spectrometer producing the infrared beam that passes through the reactive material to a detector of the spectrometer, the alteration of the reactive material allowing the spectrometer to identify and quantify the analyte.

2. The detection system of claim 1 wherein the reactive material covalently reacts with the analyte.

3. The detection system of claim 2 wherein the analyte is cyanide.

4. The detection system of claim 1 wherein the reactive material forms a coating on the substrate having a thickness within a range of from about 1 nanometer to about 20 microns.

5. The detection system of claim 1 wherein the reactive material is a metal salt.

6. The detection system of claim 1 wherein the substrate is at least partially transparent to the infrared beam.

7. The detection system of claim 1 additionally comprising a mounting structure which holds the substrate in position so that the infrared beam of the spectrometer passes through the reactive material to the detector of the spectrometer.

8. A detection system for detecting an analyte in a fluid medium comprising:
    a substrate providing mechanical stability and sized and shaped to intercept an infrared beam;
    a reactive material, coated on the substrate, that when contacted with the analyte in the fluid medium reacts with the analyte and is altered, the reaction being a chemical, biochemical or electrochemical reaction; and
    a non-ATR infrared spectrometer producing the infrared beam that passes through the reactive material to a detector of the spectrometer, the alteration of the reactive material allowing the spectrometer to identify and quantify the analyte.

9. The detection system of claim 8 wherein the reactive material covalently reacts with the analyte.

10. The detection system of claim 9 wherein the analyte is cyanide.

11. The detection system of claim 8 wherein the reactive material forms a coating on the substrate having a thickness within a range of from about 1 nanometer to about 20 microns.

12. The detection system of claim 8 wherein the reactive material is a metal salt.

13. The detection system of claim 8 wherein the substrate is at least partially transparent to the infrared beam.

14. The detection system of claim 8 additionally comprising a mounting structure which holds the substrate in position so that the infrared beam of the spectrometer passes through the reactive material to the detector of the spectrometer.

15. A detection system for detecting an analyte in a fluid medium comprising:
   a disposable substrate providing mechanical stability and sized and shaped to intercept an infrared beam;
   a reactive material, coated on the substrate, that when contacted with the analyte in the fluid medium reacts with the analyte and is altered, the reaction being a chemical, biochemical or electrochemical reaction; and
   an infrared spectrometer producing the infrared beam that passes through the reactive material to a detector of the spectrometer, the alteration of the reactive material allowing the spectrometer to identify and quantify the analyte.

16. The detection system of claim 15 wherein the reactive material covalently reacts with the analyte.

17. The detection system of claim 16 wherein the analyte is cyanide.

18. The detection system of claim 15 wherein the reactive material forms a coating on the substrate having a thickness within a range of from about 1 nanometer to about 20 microns.

19. The detection system of claim 15 wherein the reactive material is a metal salt.

20. The detection system of claim 15 wherein the substrate is at least partially transparent to the infrared beam.

21. The detection system of claim 15 additionally comprising a mounting structure which holds the substrate in position so that the infrared beam of the spectrometer passes through the reactive material to the detector of the spectrometer.

* * * * *